United States Patent [19]

Brown

[11] Patent Number: 5,552,081
[45] Date of Patent: Sep. 3, 1996

[54] DICYCLOOCTYLHALOBORANES

[75] Inventor: Herbert C. Brown, West Lafayette, Ind.

[73] Assignee: Aldrich Chemical Company, Inc., Milwaukee, Wis.

[21] Appl. No.: 304,161

[22] Filed: Sep. 12, 1994

Related U.S. Application Data

[62] Division of Ser. No. 905,115, Jun. 26, 1992, Pat. No. 5,380,940.

[51] Int. Cl.$^6$ ........................................................ C07F 5/02
[52] U.S. Cl. ........................................ 252/182.12; 562/806
[58] Field of Search ........................ 252/182.12; 562/806

[56] References Cited

U.S. PATENT DOCUMENTS

| | | | |
|---|---|---|---|
| 3,681,381 | 8/1972 | Trofimenko | 252/188.1 |
| 4,447,637 | 5/1984 | Martel et al. | 560/124 |
| 4,772,752 | 9/1988 | Brown | 568/6 |
| 4,866,181 | 9/1989 | Brown | 546/348 |
| 5,030,744 | 7/1991 | Funayama et al. | 588/12 |
| 5,043,479 | 8/1991 | Brown | 568/6 |
| 5,159,116 | 10/1992 | Brown | 568/1 |

OTHER PUBLICATIONS

Herber C. Brown et al., J. Am. Chem. Soc., 1989, III, 3441–42.
Howley, The Condensed Chemical Dictionary, 9th ed. p. 249, VuNostrond Reinhold (1977), NY.
Feiser & Feiser, *Adv. Organic Chen.*, p. 331 Reinhold Publishing Corp, 1961 New York.

*Primary Examiner*—Charles T. Jordan
*Assistant Examiner*—Anthony R. Chi
*Attorney, Agent, or Firm*—Niblack & Niblack

[57] ABSTRACT

A novel class of enolboration reagents represented by the formula $$R_2BX/R'_3N$$

wherein each R is the same or different alkyl or cycloalkyl, B is boron, X is halo, R' is lower alkyl and/indicates that $R_2BX$ is preferably employed in the presence of $R'_3N$ are disclosed. Methods of enolborating a wide variety of organic carbonyl compounds are also provided.

3 Claims, No Drawings

DICYCLOOCTYLHALOBORANES

This application is a divisional of commonly assigned, allowed application Ser. No. 07/905,115 filed Jun. 26, 1992 now U.S. Pat. No. 5,380,940.

BACKGROUND OF THE INVENTION

A. Field of Invention

The present invention relates to new reagents which facilitate the enolboration of aldehydes, ketones, carboxylic acids, anhydrides, thioesters, esters and tertiary amides and more particularly relates to novel dialkylhaloboranes.

B. Prior Art

Enolborinates are highly useful intermediates in organic synthesis. See for example: Evans et al., *J. Am. Chem. Soc.*, 1979, 101, 6120; Evans et al., Ibid., 1981, 103, 3099; Van Horn et al., *Tetrahedron Lett.*, 1979, 24, 2229; Hirama et al., Ibid., 1979, 24, 2225; Reetz et al., Ibid., 1986, 27, 4721; Hooz et al., *J. Am. Chem. Soc.*, 1968, 90, 5936; Hooz et al., Ibid., 1969, 91, 6195; Mukaiyama et al., *Chem. Lett.*, 1976, 559; Inoue et al., Ibid., 1977, 153; Mukaiyama et al., Ibid., 1979, 559; and Inoue et al., *Bull. Chem. Soc. Jpn.*, 1980, 53, 174. As a result, considerable attention has been paid in the past decade to developing simple methodologies for generating suitable organoboron derivatives, $R_2BX$, containing a good leaving group in the presence of a suitable tertiary amine.

The previously employed reagents include dialkylboron triflates, $R_2BOTf$, (Mukaiyama et al., *Chem. Lett.*, 1976, 559; Inoue et al., Ibid., 1977, 153; Mukaiyama et al., Ibid., 1979, 559; and Inone et al., *Bull. Chem. Soc. Jpn.*, 1980, 53, 174); ethylene chloroboronate (Gennari et al., *Tetrahedron Lett.*, 1984, 25, 2279); $ROBCl_2$ (Chow et al., *Helv. Chim. Acta*, 1986, 69, 604); $BCl_3$ (Chow et al., *Helv. Chim. Acta*, 1986, 69, 604); and $PhBCl_2$ (Hamana et al., *Chem. Lett.*, 1984, 1729. However, these reagents are either difficult to prepare in the pure form or only give moderate conversion to the desired enolborinates.

Further, only one organoboron reagent has been reported to date for the generation of enolborinates from esters. See Corey et al., *J. Am. Chem. Soc.*, 1990, 112, 4976; Corey et al., *Tetrahedron Lett.*, 1990, 31, 3715; Corey et al., Ibid., 1991, 32, 2857; and Corey et al., *J. Am. Chem. Soc.*, 1991, 113, 4026. Essentially no organoboron reagent is now available for the enolization of tertiary amides except for di-n-butylboron triflate, n-$Bu_2BOTf$, which has been shown to enolize a special class of reactive tertiary amides, the N,N-dialkyl-2,3,3,3-tetrafluoropropanamides. See Kuoboshi et al., *Bull. Chem. Soc. Jap.* 1990, 63, 1191; and Joshi et al., *J. Am. Chem. Soc.* 1988, 110, 6246.

I previously reported the enolboration of two ketones, diethyl ketone and propiophenone with dicyclohexylboron chloride and BCl-9-BBN. Preferential conversion into E enolates was obtained with dicyclohexylboron chloride while primarily Z enolates were obtained with BCl-9-BBN, $Chx_2BOTf$ and BOTf-9-BBN. See H. C. Brown et al, JACS, 1989, 111, 3441–3442.

We have since discovered a novel class of superior enoboration agents and have additionally discovered that dicyclohexylboron chloride is effective for the selective enolboration of carbonyl compounds other than ketones. These advances in the art were recently described in my articles which appeared as H. C. Brown et al., *JACS*, 1992, 57, 449–504 and H. C. Brown et al., Ibid., 2716–2721.

The present invention fulfills the need for enolboration agents which exhibit better selectivity and reactivity, are readily accessible and are useful in broader classes of organic compounds.

SUMMARY OF THE DISCLOSURE

The present invention provides a new class of compounds which are useful as reagents for enolboration of ketones and other carbonyl derivatives. The compounds of this invention are represented by the formula:

$$R_2BX$$

wherein each R is the same or different alkyl or cycloalkyl having from 4 to 10 carbon atoms, B is boron and X is halo with the limitations that $R_2$ may not be dicyclohexyl when X is chloro and not more than one R may have one carbon atom.

It is preferred to employ the compounds of this invention in the presence of a trialkylamine of the formula $R'_3N$ wherein and wherein each R' is the same or different lower alkyl having from 1 to 8 carbons. For ease of discussion, the reagents may also be represented by the formula:

$$R_2BX/R'_3N \text{ (or } R^TR^2BX/R'_3N\text{)}$$

indicating that the diorganohaloboranes of this invention are employed in the presence of a trialkylamine for best results.

As used herein, "halo" refers to bromo, chloro, fluoro and iodo.

The term "lower alkyl", as used herein, refers to cycloalkyl and straight or branched chain alkyl groups having from 1 to 8 carbon atoms.

The dialkylhaloboranes of this invention are most conveniently prepared by hydroboration of 2 equivalents of a corresponding olefin to $R_2BH$ with 1 equivalent of borane-methyl sulfide (BMS), followed by addition of the appropriate XH or $X_2$. Alternatively, the compounds of this invention may be prepared directly from the corresponding olefin by hydroboration with a monohaloborane. The latter method is especially useful in cases where the hydroboration fails to stop cleanly at the dialkylborane stage.

The above methods are shown in the following reactions schemes.

$$R \xrightarrow{BH_3 \cdot SMe_2} R_2BH \xrightarrow{HX} R_2BX + H_2$$

$$R \xrightarrow{XBH_2 \cdot SMe_2} R_2BX$$

wherein R is the desired alkene, for example, cyclohexene.

Since the hydroboration of norbornene and cyclooctene with BMS proceeds rapidly past the desired $R_2BH$ intermediates to the trialkylboranes, these alkenes are preferably hydroborated with monochloroborane to obtain the desired dialkylchloroboranes.

The novel compounds of the present invention are useful to achieve enolboration of a wide variety of organic compounds including ketones, carboxylic acids, anhydrides, aldehydes, esters and tertiary amides.

The enolization of a broad range of carbonyl compounds by the process of this invention is represented by the following illustrative reaction sequence using dicyclohexy-lchloroborane in the presence of triethylamine.

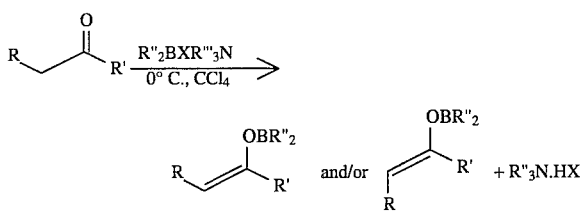

R=H, alkyl or aryl

R'=H, alkyl, aryl, N-dialkyl, N-diaryl, O-alkyl, O-aryl, S-alkyl, or S-aryl

R"=alkyl or cycloalkyl

R'"=alkyl

X=Cl, Br or I

DETAILED DESCRIPTION OF PREFERRED EMBODIMENTS

In the following examples, all glassware used were thoroughly dried in an oven and cooled and assembled under a stream of nitrogen. Degassed and anhydrous solvents, $CCl_4$, $CH_2Cl_2$, benzene and hexane were used. THF was freshly distilled from sodium benzophenone ketyl. $Et_3N$ was used after distilling over $CaH_2$. All alkenes, ketones, aldehydes, carboxylic acids, anhydrides, esters, amides, thioesters and β-keto esters were commercial products of the highest purity available. Whenever necessary, commercially available liquid olefins were purified by distillation over $LiAlH_4$ and ketones over $CaH_2$. Borane-methyl sulfide (BMS) and monochloroborane-methyl sulfide (MCBS) reagents were purchased from Aldrich Chemical Company, Inc., Milwaukee, Wis.

$^1$H NMR spectra were recorded on T-60-, 200- and 300 MHz instruments. $^{11}$B NMR spectra were recorded on FT-80A and 300-MHz instruments. The chemical shift values are in δ (ppm) relative to $BF_3.OEt_2$.

EXAMPLE 1

Preparation of Dicyclohexylchloroborane

A 500-mL round-bottom flask capped with a rubber septum, a magnetic stirring bar, and a connecting tube attached to a mercury bubbler was charged with diethyl ether (150 mL) and cyclohexene (41 mL, 400 mmol). The flask was cooled in an ice bath, borane-methyl sulfide (BMS, 20 mL, 200 mmol) was added slowly, and stirring was continued for 3 h at 0° C. Dicyclohexylborane precipitated as a white solid. The supernatant liquid was removed by a double-ended needle, the solid was washed with ether, and the liquid was removed. Then the solid was suspended in 100 mL of diethyl ether, and anhydrous HCl in ether (66.7 mL of 3M solution, 200 mmol) was added slowly to the suspension at 0° C. Hydrogen is rapidly evolved and should be safely vented. A clear solution was obtained. The $^{11}$B NMR analysis of the resulting solution showed formation of $Chx_2BCl$ (δ 66 ppm in diethyl ether). Distillation provides the pure title product (δ 76 ppm in hexane), 31.6 g, 75% yield, bp 95°–96 ° C. (0.35 mm).

EXAMPLE 2

Preparation of B-chloro-9-borabicyclo[3.3.1]nonane

The title compound was prepared in 75% yield following the method of Example 1 by treating 9-borabicyclo[3.3.1]nonane (9-BBN, Aldrich Chemical Company, Inc., Milwaukee, Wis.) with anhydrous HCl in ether. $^{11}$B NMR δ 79 ppm in hexane, bp 65° C. (0.3 mm).

EXAMPLE 3

Preparation of disiamylchloroborane ($Sia_2BCl$)

Following a procedure similar to Example 1, the title compound was prepared in 75% yield from 2-methyl-2-butene. $^{11}$B NMR, δ 78 ppm in hexane.

EXAMPLE 4

Preparation of bis(2,5-dimethylcyclohexyl) chloroborane (2,5-$Me_2Chx_2BCl$)

The title compound was prepared in 70% yield by the method of Example 1 from 2,5-dimethylcyclohexene. $^{11}$B NMR, δ 74 ppm in ether.

EXAMPLE 5

Alternate Synthesis of Dialkylchloroboranes

The following synthesis of dicyclohexylchloroborane ($Chx_2BCl$) is representative of the alternate process of this invention of synthesizing a dialkylchloroborane via hydroboration of an alkene with monochloroborane-methyl sulfide.

A 250-mL round bottom flask fitted with a rubber septum, a magnetic stirring bar, and a connecting tube attached to a mercury bubbler was cooled in an ice bath and charged with diethyl ether (90 mL) under inert atmosphere. Cyclohexene (21.2 mL, 210 mmol) was added, followed by the slow addition of monochloroborane-methyl sulfide (11.6 mL, 100 mmol). The mixture was stirred at 0° C. for 2 h. The solvent was removed under reduced pressure (25° C., 12 Torr). Distillation provided pure dicyclohexylchloroborane (δ 76 ppm in hexane), 16.85 g, 80% yield, bp 104°–105° C. (0.5 mm). Synthesis of this product by this process can readily be carried out on a molar scale.

Bis(exo-norbornyl)chloroborane and dicyclooctylchloroborane were prepared using the above procedure.

The following examples illustrate the enolization of various classes of organic compounds using diorganochloroborane in the presence of triethylamine.

EXAMPLE 6

General Procedure for the Enolboration of Ketones

To a stirred solution of dicyclohexylchloroborane (5.2 mmol) and triethylamine (0.73 mL, 5.2 mmol) in carbon tetrachloride (20 mL) cooled at 0° C. was added dropwise 2-butanone (5 mmol). Enolborinate was generated instantaneously with concurrent formation and precipitation of triethylamine hydrochloride. An internal standard, benzene (0.5 mmol), was added for quantification of the enolborinate by $^1$H NMR analysis. Molarity was adjusted around 0.2–0.3M. The reaction mixture was stirred for the desired length of time and transferred into a centrifuge vial through a double-ended needle (18 gauge). Centrifugation resulted in the separation of the enolborinate solution from $Et_3N.HCl$, which was transferred into an NMR tube via a double-ended needle. $^1$H NMR and $^{11}$B NMR analyses showed the extent of enolization.

EXAMPLES 7–11

Regioselective Enolboration of 2-Butanone with various $R_2BCl/Et_3N$ Reagents Enolboration of 2-butanone was carried out according to the procedure of example 6 using: (1) B-chloro-9-borabicyclo[3.3.1]nonane (B-Cl-9-BBN); (2) bis(exo-norbornyl)chloroborane (exo-Nrb$_2$BCl); (3) dicyclooctylchloroborane (Coc$_2$BCl); (4) dicyclohexylchloroborane (Chx$_2$BCl); (5) disiamylchloroborane (Sia$_2$BCl); and (6) bis(2,5-dimethylcyclohexyl)chloroborane (2,5-Me$_2$Chx$_2$BCl). Enolizations were carried out in CCl$_4$ at 0° C. unless otherwise stated using benzene as the internal standard. Both $^1$H NMR (olefinic proton) and $^{11}$B NMR (borinate region) were used to determine the extent of enolization. Examination of the reaction product mixture (olefinic proton) by $^1$H NMR also revealed the regioselectivity of the enolization. The two olefinic protons of the terminal enolate (on the methyl side) appear as two singlets at δ 4.2 and 4.4 ppm, and the olefinic proton of the internal enolate (on the ethyl side) appears as a quartet at δ 4.7–5.0 ppm. The enolization of 2-butanone is represented by the following reaction scheme:

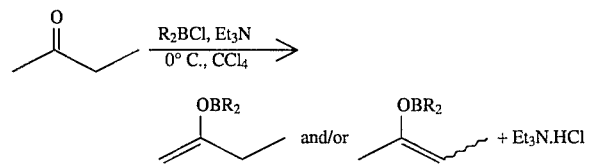

The results are summarized in Table I.

TABLE I

Regioselective Enolboration or 2-Butanone with Various $R_2BCl/Et_3N^a$

| $R_2BCl$ | time (min) | % enolborinate[b] | % regioisomer[c] | |
|---|---|---|---|---|
| | | | terminal | internal |
| 1 | 30 | 95 | 67 | 33 |
| 2 | 30 | 97 | 99 | 1 |
| 3 | 30 | 97 | 99 | 1 |
| 4 | 30 | 98 | 99 | 1 |
| 5 | 30 | 95 | 99 | 1 |
| 6[d] | 45 | 92 | 99 | 1 |

[a]Reactions were carried out in CCl$_4$ at 0° C. unless otherwide stated. [b]Determined by $^1$H NMR using benzene as an internal standard and $^{11}$B NMR. [c]Determined by $^1$H NMR. [d]Reaction at 25° C.

EXAMPLES 12–17

Regioselective Enolboration of 3-Pentanone with various $R_2BCl/Et_3N$ Reagents After establishing the regioselectivity and reactivity of various $R_2BCl$ reagents toward an unsymmetrical ketone, 2-butanone, enolboration of a representative symmetrical ketone, 3-pentanone, was carried out according to the procedure of example 6 using: (1) B-Cl-9-BBN; (2) exo-Nrb$_2$BCl; (3) Coc$_2$BCl; (4) Chx$_2$BCl; (5) Sia$_2$BCl; and (6) 2,5-Me$_2$Chx$_2$BCl. Reactions were carried out in CCl$_4$ at 0° C. unless otherwise stated. The results are summarized in Table II.

TABLE II

Enolboration of 3-Pentanone with Various $R_2BCl/Et_2N^a$

| $R_2BCl$ | time (min) | % enolborinate[b] |
|---|---|---|
| 1 | 30 | 95 |
| 2 | 30 | 96 |
| 3 | 30 | 97 |
| 4 | 30 | 96 |
| 5 | 90 | 32 |
| 6[c] | 45 | 25 |

[a]Reactions were carried out in CCl$_4$ at 0° C. unless otherwise stated. [b]Determined by $^1$H NMR using benzene an an internal standard and $^{11}$B NMR. [c]Reaction at 0° C.

EXAMPLE 18

Representative Enolboration of Aldehydes

A stirred solution of Chx$_2$BCl (1.2 mL, 5.5 mmol) and Et$_3$N (0.77 mL, 5.5 mmol) in CCl$_4$ (15 mL) was cooled to 0° C. and then phenylacetaldehyde in CCl$_4$ (5 mL of 1M solution, 5 mmol) was added dropwise over a 20–30 minute period. An immediate precipitate of triethylamine hydrochloride occurred, suggesting a fast reaction. The reaction mixture was stirred at 0° C. for ½ hr and worked up as described previously for ketones. Analysis by $^1$H NMR and $^{11}$B NMR suggests >95% enolation.

EXAMPLES 19–21

Following the method of Example 18, enolboration of n-butyraldehyde, cyclohexanecarboxaldehyde and isobutyraldehyde were carried out. Table III summarizes the enolboration of simple aldehydes according to the present invention.

TABLE III

Enolboration of Simple Aldehydes with Chx$_2$BCl/Et$_3$N$^a$

| Aldehyde | Time (min) | enolborinate | $^{11}$B NMR[b] (δ ppm) | $^1$H NMR[c] (δ ppm) | % enolborinate[d] |
|---|---|---|---|---|---|
| CH$_3$CH$_2$CH$_2$CHO | 30 | CH$_3$CH$_2$CH=CH(OBChx$_2$) | 53 | 4.5–4.78(m) and 6.58(d, J=6.8Hz) | 95 |
| PhCH$_2$CHO | 30 | PhCH=CH(OBChx$_2$) | 52 | 5.45(d, J=6.8Hz) and 6.70(d, J=6.8Hz) | 95 |
| (CH$_3$)$_2$CHCHO | 45 | (CH$_3$)$_2$C=CH(OBChx$_2$) | 53 | 6.38(s, 1H) | 94 |

TABLE III-continued

| | | Enolboration of Simple Aldehydes with $Chx_2BCl/Et_3N^a$ | | | |
|---|---|---|---|---|---|
| Aldehyde | Time (min) | enolborinate | $^{11}B$ $NMR^b$ ($\delta$ ppm) | $^{1}H$ $NMR^c$ ($\delta$ ppm) | % enol-borinate$^d$ |
| 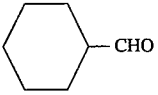—CHO | 45 | 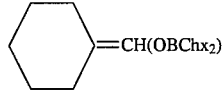=CH(OBChx$_2$) | 54 | 6.38(s, 1H) | 94 |

$^a$Reactions were carried out in $CCl_4$ at 0° C. $^{b\,11}B$ NMR observed as a broad singlet. $^c$Olefinic proton(s). $^d$Determined by $^{1}H$ and $^{11}B$ NMR.

EXAMPLE 22

Representative Enolboration of Carboxylic Acids and Derivatives

To a stirred solution of $Chx_2BCl$ (2.4 mL, 11 mmol, 2.1 equiv) and $Et_3N$ (1.54 mL, 11 mmol, 2.1 equiv) in $CCl_4$ (50 mL) cooled to 0° C. was added an internal standard, benzene (0.5 mmol). The molarity of the solution was adjusted to 0.2M with respect to $R_2BCl$. Then propionic acid (0.38 mL, 5 mmol, 1 equiv) was added dropwise. An immediate precipitation of $Et_3N$.HCl occurred, suggesting a fast reaction. The reaction mixture was stirred at 0° C. for 1 h and worked up as described previously for ketones. Analysis of the olefinic protons by $^{1}H$ NMR suggests >95% enolization of the acid.

EXAMPLE 23-28

Following the method of Example 22, caproic acid, phenylacetic acid, propionic anhydride, S-tert-butyl thioacetate, S-phenyl thioacetate and ethyl acetoacetate were successfully enolized. The results of these representative enolborations is set forth below in Table IV.

TABLE IV

| | | Enolboration of Carboxylic Acids and Derivatives With $Chx_2BCl/Et_34N^a$ | | | |
|---|---|---|---|---|---|
| carbonyl compound | time (min) | enolborinate | $^{11}B$ $NMR^b$ ($\delta$ ppm) | $^{1}H$ $NMR^c$ ($\delta$ ppm) | % enolborinate$^d$ |
| acids$^e$ | | | | | |
| $CH_3CH_2COOH$ | 60 | $CH_2CH=C(OBChx_2)_2$ | 50 | 4.18(q, J=6.8Hz) | 97 |
| $CH_3(CH_2)_4COOH$ | 60 | $CH_3(CH_2)_3CH=C(OBChx_2)_2$ | 51 | 4.10(t, J=7.1Hz) | 95 |
| $PhCH_2COOH$ | 60 | $PhCH=C(OBChx_2)_2$ | 50 | 5.40(s) | 98 |
| anhydrides $(CH_3CH_2CO)_2O$ | 60 | $CHCH=C(OBChx_2)OCOC_2H_5$ | 50 | 4.9(q) | 90 |
| acid chlorides$^f$ | | no enolization | | | |
| esters$^f$ | | no enolization | | | |
| amides$^f$ | | no enolization | | | |
| thioesters$^g$ | | | | | |
| $CH_3COSC(CH_3)_3$ | 60 | $CH_2=C(OBChx_2)SC(CH_2)_3$ | 52 | 4.85(s, 1H), 4.95(s, 1H) | 95 |
| $CH_3COSPh$ | 30 | $CH_2=C(OBChx_2)SPh$ | 50 | 4.62(s, 1H), 4.73(s, 1H) | 90 |
| β-keto ester $CH_3COCH_2CO_2C_2H_5$ | 60 | $CH_3C(OBChx_2)=CHCO_2C_2H_6$ | 15 | 4.68(s, 1H) | 94 |

$^a$Reactions were carried out in $CCl_4$ at 0° C. unless otherwise stated. $^{b\,11}B$ NMR observed as broad singlet. $^c$Olefinic proton(s). $^d$Determined by $^{1}H$ and $^{11}B$. $^e$Enolication with 2 equiv. of reagents. $^f$Enolization at 25° C.

The enolate geometry of enolborinates from representative carbonyl compounds is set forth in Table V below.

TABLE V

Enolate Geometry of the Enolborinates from Representative Carbonyl Compounds

| carbonyl compound | $^1$H NMR$^a$ ($\delta$ ppm) syn | anti | % enolate$^b$ Z | E | % yield$^c$ |
|---|---|---|---|---|---|
| CH$_2$CH$_2$COCH$_2$CH$_3$ | 5.01(d, J=4.4Hz) | 4.72 (d, J=8.4 Hz) | 21 | 79 | 95 |
| PhCOCH$_2$CH$_3$ | 5.08(d, J=4.0Hz) | 4.88(d, J=8.0Hz) | <1 | >99 | 87 |
| PhCH$_2$CHO$^d$ | — | — | 67 | 33 | 95 |
| CH$_3$CH$_2$COOH | 5.17(d, J=3.8Hz) | 4.73 (d, J=9.1 Hz) | 18 | 82 | 95 |
| PhCH$_2$COOH | — | 5.20(d, J=10.0Hz)$^e$ | <1 | >90 | 95 |
|  | — | 3.90(d, J=10.0Hz)$^f$ |  |  |  |
| (CH$_3$CH$_2$CO)$_2$O | 5.14(d, J=3.9Hz) | 4.71(d, J=8.7Hz) | 29 | 71 | 85 |

$^a$Corresponds to the benzylic proton of the aldol products with benzaldehyde. $^b$Based on the syn/anti ratio. $^c$Determined by $^1$H NMR analysis (not isolated yield). $^d$Directly determined from the enolborinate; see text for $^1$H NMR data. $^e$Corresponds to the benzylic proto $\alpha$ to OH of the aldol. $^f$Corresponds to the benzylic proton $\alpha$ to COOH of the aldol.

Methyl ketones, ethyl ketones, isopropyl ketones, $\alpha,\beta$-unsaturated ketones, cyclic ketones, bicyclic ketones, heterocyclic ketones and aromatic ketones have been successfully enolborated according to this invention as well as other carbonyl derivatives including aldehydes, carboxylic acids, anhydrides and thioesters.

The stereoselective enolboration of propiophenone illustrates the exceptional properties of the compounds of this invention. Earlier literature reveals that with prior art reagents and methods, enolboration of propiophenone gave the Z borinate predominately. The highest reported conversion to the E enolborinate was that for the enolboration of propiophenone with R$_2$BOTf of only 3%. In the practice of this invention, propiophenone was converted almost exclusively to the E enolborinate.

As described further below, both aliphatic and aromatic esters and tertiary amides have been enolized employing the reagents and processes of the present invention.

EXAMPLE 29

Preparation of Dicyclohexyliodoborane (Chx$_2$BI)

To a suspended solution of dicyclohexylborane (22.3 g, 125.3 mmol) in hexane (100 mL) at 0° C. under a nitrogen atmosphere, solid I$_2$ (15.95, 62.84 mmol) was added through a side arm in small installments with constant stirring. Hydrogen is evolved and should be safely vented. After adding all the iodine, the reaction mixture is stirred at 0° C. for 2 h and at 25 0° C. for 1 h. A pale pink color persisted which shows the completion of the reaction. The solvent was removed by a water aspirator (20 mm). Distillation of the concentrated mixture under vacuum yielded pure, colorless dicyclohexyliodoborane, bp 198°–200° C. (1.25 mm), 80% yield, $^{11}$B NMR (hexane) $\delta$ 84 ppm.

EXAMPLE 30

General Method for Enolboration of Esters and Tertiary Amides

To a stirred solution of dicyclohexyliodoborane (1.1 mL, 5.15 mmol) and triethylamine (5.15 mmol) in CCl$_4$ (15 mL) kept at the required temperature under N$_2$ atmosphere, the ester or tertiary amide (5.0 mmol) is added dropwise. The enolborinate is generated instantaneously with concurrent formation and precipitation of triethylamine hydroiodide. An internal standard, benzene (0.50 mL, 1.00M in CCl$_4$, 0.50 mmol) is added (except for the aromatic compounds) for quantification of the enolborinate. The reaction mixture is stirred for 2 h at the same temperature and transferred into a centrifuge vial through a double-ended needle (18 gauge). Centrifugation results in the separation of the enolborinate solution from the solid Et$_3$N.HI. In representative cases, this solid was collected and weighed. Essentially quantitative yields are obtained. The enolborinate solution is then transferred into an NMR tube by a double-ended needle. The $^1$H NMR (olefinic proton) analysis gives the extent of enolization and the $^{11}$B NMR spectrum (borinate region, usually broad, 50–56 ppm) confirms the formation of enolborinates. In representative cases, the enolborinates were treated with benzaldehyde and the enolates proved to be highly reactive even at –78° C.

Chx$_2$BI is easy to prepare and very stable even at room temperature under an inert atmosphere. No cleavage of ester has been observed. The reaction is essentially instantaneous, even at 0° C. in all cases except for the sterically hindered tert-butyl propionate. Visual observation of the formation of Et$_3$N.HI as a pale yellow precipitate as the enolization progresses is an added advantage for this reagent, providing a convenient guide to the course of the reaction. Chx$_2$BI thus has proved to be a valuable, practical reagent for the enolization of ester and teriary amides and has achieved for the first time the facile enolization of these organic compounds.

EXAMPLES 31–39

Nine representative esters and tertiary amides were enolborated following the method of Example 30. The results are set forth in Table VI below.

TABLE VI

Enolboration of Esters and Tertiary Amides with Chx$_2$BI in the Presence of Different Amines$^a$

| Ester/Amide | Amine | $^1$H NMR ($\delta$ ppm)$^b$ | Yield$^{c,d}$ |
|---|---|---|---|
| MeCH$_2$COOEt | Et$_3$N | 3.97(q, J=7.2Hz) | 96 |
|  | i-Pr$_2$EtN |  | 70 |
| PhCH$_2$COOEt | Et$_3$N | 4.84(s) | 96 |
|  | i-Pr$_2$EtN |  | 95 |
| EtCH$_2$COOEt | Et$_3$N | 3.96(t, J=7.1Hz) | 95 |
| i-PrCH$_2$COOEt | Et$_3$N | 3.60(d, J=8.7Hz) | 94 |
| t-BuCH$_2$COOEt | Et$_3$N | 3.59(s) | 84 |
| MeCH$_2$COOCMe$_3$ | Et$_3$N | 4.11(q, J=6.7Hz) | 60 |
|  | Et$_3$N$^e$ |  | 87 |
|  | i-Pr$_2$EtN |  | 57 |
|  | i-Pr$_2$EtN$^e$ |  | 74 |
| MeCH$_2$CONMe$_2$ | Et$_3$N | 4.59(q, J=6.7Hz) | 96 |

TABLE VI-continued

Enolboration of Esters and Tertiary Amides with Chx$_2$BI in the Presence of Different Amines[a]

| Ester/Amide | Amine | $^1$H NMR (δ ppm)[b] | Yield[c,d] |
|---|---|---|---|
| PhCH$_2$CONMe$_2$ | i-Pr$_2$EtN | | 86 |
| | Et$_3$N | 4.20(s) | 96 |
| | i-Pr$_2$EtN | | 93 |
| MeCH$_2$CONEt$_2$ | Et$_3$N | 3.45(q, J=7.1Hz) | 94 |
| | i-Pr$_2$EtN | | 83 |

[a]Reactions were carried out in CCl$_4$ at 0° C. unless otherwise stated. [b]Corresponds to the olefinic protons of the enolborinates. [c]Based on the $^1$H NMR by comparing the integration of the olefinic proton of the enolborinate with those of the internal standard benzene (the estimated error limit ± 3%). [d]In representative cases, the NMR yields were also confirmed by collecting and weighing the solid Et$_3$N.HI. [e]Enolization at 25° C.

The following tables summarize the results of extensive studies of the enolboration of various classes of ketones with dicyclohexylchloroborane in the presence of triethylamine.

TABLE VII

Enolboration of Methyl Ketones with Chx$_2$BCl/Et$_3$N[a]

| RCOR' | | time | enolborinate | $^{11}$B NMR[b] | $^1$H NMR[c] | % enol- |
|---|---|---|---|---|---|---|
| R | R' | (min) | | (δ ppm) | (δ ppm) | borinate[d] |
| Me | Me | 30 | CH$_2$=C(OBChx$_2$)Me | 51 | 4.18(s, 1H), 4.30(s, 1H) | 100 |
| Me | Et | 30 | CH$_2$=C(OBChx$_2$)Et | 51 | 4.12(s, 1H), 4.25(s, 1H) | 97 |
| Me | Pr | 30 | CH$_2$=C(OBChx$_2$)Pr | 52 | 4.18(s, 1H), 4.28(s, 1H) | 97 |
| Me | i-Pr | 30 | CH$_2$=C(OBChx$_2$)i-Pr | 53 | 4.10(s, 1H), 4.30(s, 1H) | 96 |
| Me | i-Bu | 30 | CH$_2$=C(OBChx$_2$)i-Bu | 52 | 4.20(s, 1H), 4.29(s, 1H) | 95 |
| Me | neo-pen | 30 | CH$_2$=C(OBChx$_2$)neo-pen | 53 | 4.28(s, 2H) | 95 |
| Me | Ph | 40 | CH$_2$=C(OBChx$_2$)Ph | 50 | 5.55(s, 1H), 5.12(s, 1H) | 95 |

[a]Reactions were carried out in CCl$_4$ at 0° C. unless otherwise stated. [b]$^{11}$B NMR observed as a broad singlet. [c]Olefinic proton(s). [d]Determined by $^1$H and $^{11}$B NMR.

TABLE VIII

Enolboration of Ethyl Ketones with Chx$_2$BCl/Et$_3$N[a]

| RCOR' | | time | enolborinate | $^{11}$B NMR[b] | $^1$H NMR[c] | % enol- |
|---|---|---|---|---|---|---|
| R | R' | (h) | | (δ ppm) | (δ ppm) | borinate[d] |
| Et | Et | 0.5 | CH$_3$CH=C(OBChx$_2$)Et | 53 | 4.65(q, 1H, J=6.3Hz) | 97 |
| Et | i-Pr | 0.5 | CH$_3$CH=C(OBChx$_2$)i-Pr | 54 | 4.67(q, 1H, J=6.5Hz) | 95 |
| Et | i-Bu | 0.5 | CH$_3$CH=C(OBChx$_2$)i-Bu | 54 | 4.64(q, 1H, J=6.3Hz) | 93 |
| Et | t-Bu | 46[e] | CH$_3$CH=C(OBChx$_2$)t-Bu | 54 | 4.65(q, 1H, J=6.4Hz) | 60 |
| Et | Chx | 0.5 | CH$_3$CH=C(OBChx$_2$)Chx | 54 | 4.60(q, 1H, J=6.6Hz) | 94 |
| Et | Ph | 1.0 | CH$_3$CH=C(OBChx$_2$)Ph | 52 | 5.10(q, 1H, J=7.4Hz)[f] | 90 |

[a]Reactions were carried out in CCl$_4$ at 0° C. unless otherwise stated. [b]$^{11}$B NMR observed as a broad singlet. [c]Olefinic proton(s). [d]Determined by $^1$H and $^{11}$B NMR. [e]Enolization at 25° C. [f]Corresponds to [E]-enolate; its [Z]-enolate, obtained after isomerization, appeared at δ 5.5 ppm (q, J=7.4Hz).

TABLE IX

Enolboration of Sterically Hindered Ketones with Chx$_2$BCl/Et$_3$N[a]

| ketone | time (h) | % enolborinate[b] |
|---|---|---|
| Me$_2$CHCOCHMe$_2$ | 1.0 | <1 |
| Me$_2$CHCOCHMe$_2$ | 24[c] | 10 |
| Me$_2$CHCOPh | 1.0 | <1 |
| Me$_2$CHCOCpn | 1.0 | <1 |
| 2,5-dimethylcyclopentanone | 1.0 | <1 |
| 2,6-dimethylcyclohexanone | 1.0 | <1 |

[a]Reactions were carried out in CCl$_4$ at 0° C. unless otherwise stated. [b]Determined directly by $^{11}$B NMR of the enolborinate and indirectly by $^1$H NMR of its benzaldehyde aldol product. [c]Enolization at 25° C.

TABLE X

Enolboration of α,β-Ketones with CHx₂BCl/Et₃N[a]

| ketone | time (min) | enolborinate | ¹¹B NMR[b] (δ ppm) | ¹H NMR[c] (δ ppm) | % enolborinate[d] |
|---|---|---|---|---|---|
| cyclohex-2-enone | 60 | OBChx₂ (cyclohexadienyl) | 52 | 5.1(t, 1H) | 85 |
| methyl vinyl ketone | 60 | OBChx₂ (diene) | 53 | 4.4(s, 1H), 4.5(s, 1H) | 65 |
| 4-phenyl-3-butyn-2-one | 30 | OBChx₂ (Ph-ynenyl) | 51 | 4.9(s, 1H), 5.0(s, 1H) | 90 |

[a]Reactions were carried out in CCl₄ at 0° C. unless otherwise stated. [b]¹¹B NMR observed as a broad singlet. [c]Olefinic proton(s) of the enolate double bond. [d]Determined by ¹H and ¹¹B NMR.

TABLE XI

Enolboration of Cyclic Ketones with Chx₂BCl/Et₃N[a]

| ketone | time (min) | enolborinate | ¹¹B NMR[b] (δ ppm) | ¹H NMR[c] (δ ppm) | % enolborinate[d] |
|---|---|---|---|---|---|
| cyclopentanone | 35[e] | OBChx₂ | 53 | 4.80(s, br) | 98 |
| cyclohexanone | 45 | OBChx₂ | 53 | 4.92(t, br) | 98 |
| cycloheptanone | 30 | OBChx₂ | 54 | 4.95(t, J=5.8Hz) | 96 |
| cyclooctanone | 30 | OBChx₂ | 54 | 4.85(t, J=5.8Hz) | 96 |
| 2-methylcyclohexanone | 45 | OBChx₂ | 52 | 4.87(t, br) | 95 |

TABLE XI-continued

Enolboration of Cyclic Ketones with $Chx_2BCl/Et_3N$[a]

| ketone | time (min) | enolborinate | $^{11}B$ NMR[b] (δ ppm) | $^1H$ NMR[c] (δ ppm) | % enol-borinate[d] |
|---|---|---|---|---|---|
| 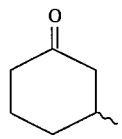 | 45 | 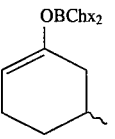 | 50 | 4.80(t, br) | 95 |

[a]Reactions were carried out in $CCl_4$ at 0° C. unless otherwise stated. [b]$^{11}B$ NMR observed as a broad singlet. [c]Olefinic proton(s). [d]Determined by $^1H$ and $^{11}B$ NMR. [e]Enolization at 25° C.

TABLE XII

Enolboration of Bicyclic and Heterocyclic Ketones with $Chx_2BCl/Et_3N$[a]

| ketone | time (min) | enolborinate | $^{11}B$ NMR[b] (δ ppm) | $^1H$ NMR[c] (δ ppm) | % enol-borinate[d] |
|---|---|---|---|---|---|
| 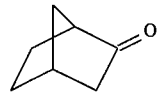 | 30[e] | 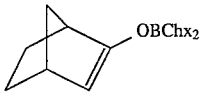 | 53 | 4.85(d, J=3.4Hz) | 96 |
| 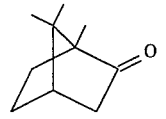 | 30[e] | 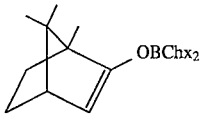 | 53 | 4.82(d, J=3.4Hz) | 92 |
| 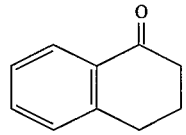 | 45 | 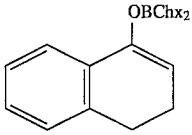 | 52 | 5.22(t, J=4.0Hz) | 95 |
| 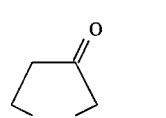 | 30[f] | 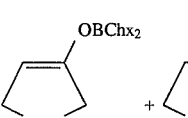 | 54 | I: 5.10(s, br) <br> II: 5.28(s, br) | 90 |
| 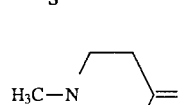 | 60[g] | 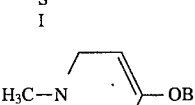 | 53 | 4.95(s, br) | 70 |

[a]Reactions were carried out in $CCl_4$ at 0° C. unless otherwise stated. [b]$^{11}B$ NMR observed as a broad singlet. [c]Olefinic proton(s). [d]Determined by $^1H$ and $^{11}B$ NMR. [e]Enolization at 25° C.. [f]Regioisomers I:II = 60:40. [g]Enolization without $Et_3N$.

TABLE XIII

Enolboration of Aromatic Ketones with $Chx_2BCl/Et_3N$[a]

| RCOR' | | time (min) | enolborinate | $^{11}B$ NMR[b] (δ ppm) | $^1H$ NMR[c] (δ ppm) | % enol-borinate[d] |
|---|---|---|---|---|---|---|
| R | R' | | | | | |
| Ph | Me | 40 | $CH_2$=$C(OBChx_2)$Ph | 50 | 4.55(s, 1H), 5.12(s, 1H) | 95 |
| Ph | Et | 60 | $CH_3CH$=$C(OBChx_2)$Ph | 52 | 5.10(q, J=7.4Hz) | 90 |
| Bn | Me | 60 | $CH_2$=$C(OBChx_2)$Bn | 52 | 4.20(s, 1H), 4.40(s, 1H) | 95 |

TABLE XIII-continued

Enolboration of Aromatic Ketones with $Chx_2BCl/Et_3N^a$

| RCOR' | | time (min) | enolborinate | $^{11}B$ $NMR^b$ (δ ppm) | $^1H$ $NMR^c$ (δ ppm) | % enol- borinate$^d$ |
|---|---|---|---|---|---|---|
| R | R' | | | | | |
| | | | PhCH=C(OBChx$_2$)Me | | 5.68(s, 1H) | |
| Bn | Et | 60 | PhCH=C(OBChx$_2$)Et | 52 | 5.73(s, 1H), 5.59(s. 1H) | 94 |
| Bn | Ph | 60 | PhCH=C(OBChx$_2$)Ph | 53 | 6.40(s, 1H), 6.20(s, 1H) | 92 |
| Bn | i-Pr | 60 | PhCH=C(OBChx$_2$)i-Pr | 52 | 5.60(s, 1H) | 90 |

$^a$Reactions were carried out in $CCl_4$ at 0° C. unless otherwise stated. $^{b11}B$ NMR observed as a broad singlet. $^c$Olefinic proton(s). $^d$Determined by $^1H$ and $^{11}B$ NMR.

TABLE XIV

Results of Enolate Geometry of the Enolborinates Derived From Various Ethyl and Benzyl Ketones using $Chx_2BCl/Et_3N$

| RCOR" | | $^1H$ $NMR^a$ (δ ppm) | | % enolate$^b$ | | % yield$^c$ |
|---|---|---|---|---|---|---|
| R | R' | syn/[Z] | anti/[E] | [Z] | [E] | |
| Et | Et | 5.01(d, J=4.4Hz) | 4.72(d, J=8.4Hz) | 21 | 79 | 97 |
| Et | i-Pr | 4.63(d, J=6.0Hz) | 4.43(d, J=8.6Hz) | <1 | >99 | 90 |
| Et | i-Bu | 5.00(d, J=4.5Hz) | 4.71(d, J=8.2Hz) | 12 | 88 | 90 |
| Et | t-Bu | 4.80(d, J=4.0Hz) | 4.68(d, J=8.0Hz) | <1 | >99 | 56 |
| Et | Chx | 4.81(d, J=5.0Hz) | 4.63(d, J=8.0Hz) | <1 | >99 | 90 |
| Et | Ph | 5.08(d, J=4.0Hz) | 4.88(d, J=8.0Hz)) | <1 | >99 | 87 |
| Bn | Me | 5.68(s, 1H) | — | >99 | <1 | 91 |
| Bn | Et | 5.73(s, 1H) | 5.59(s, 1H) | 60 | 40 | 90 |
| Bn | Ph | 6.40(s, 1H) | 6.20(s, 1H) | 20 | 80 | 88 |
| Bn | i-Pr | — | 5.60(s, 1H) | <1 | >99 | 87 |

$^a$Corresponds to the benzylic proton of the benzaldehyde aldol products in the case of ethyl ketones and to the olefinic proton(s) of the enolborinate in the case of benzyl ketones. $^b$Based on the syn/anti ratio in the case of ethyl ketones. $^c$Determined from the $^1H$ NMR (not isolated yield).

EXAMPLE 40

Preparation of bis(bicyclo[2.2.2]octyl)chloroborane ($Bco_2BCl$)

The title compound was prepared by the method of Example 1 from bicyclo[2.2.2]oct-2-ene. The resulting $Bco_2BCl$ (>98% pure based on $^{11}B$ NMR, δ80 ppm in ether) is a colorless liquid and can be used directly since it decomposes on attempted distallation at 0.1 mm.

Upon reaction with ketones, $Bco_2BCl$ achieves the E enolborinates with a selectivity equal to or higher than that achieved with $Chx_2BCl$. Table XV illustrates this observation.

TABLE XV

Comparison of $Bco_2BCl/Et_3N/Et_3N$ for the Stereoselective Enolboration of Various Ketones

| RCOR' | | $ChxBCl^b$ (%) | | | $Bco_2BCl^b$ (%) | | |
|---|---|---|---|---|---|---|---|
| R | R' | Z | E | yield$^c$ | Z | E | yield |
| Et | i-Pr | <3 | >97 | 95 | <3 | >97 | 94 |
| Et | Chx | <3 | >97 | 96 | <3 | >97 | 95 |
| Et | t-Bu | <3 | >97 | 60 | <3 | >97 | 55$^d$ |
| Et | Ph | <3 | >97 | 92 | <3 | >97 | 90 |
| Et | Et | 21 | 79 | 95 | 3 | 97 | 90 |
| Et | i-Bu | 17 | 83 | 96 | 11 | 89 | 94 |
| n-Pr | n-Pr | 20 | 80 | 95 | <3 | >97 | 94 |
| n-Bu | n-Bu | 29 | 71 | 95 | <3 | >97 | 93 |

$^a$Reactions were carried out in $CCl_4$ at 0° C. unless otherwise stated. $^b$Z/E ratio was determined based on the syn/anti ratio of their corresponding benzaldehyde aldol products. $^c$Determined by $^1H$ NMR. $^d$Reaction at 25° C.

Reference to "alkyl" herein refers to both straight and branched chain alkyl.

From the foregoing, it will be apparent to those skilled in the art that the above examples are illustrative and that modifications may be made without departing from the spirit and scope of the claims.

We claim:

1. An enoboration agent represented by the formula:

$R_2BX/R'_3N$ wherein each R is, cyclooctyl, B is boron, X is halo, R' is lower alkyl and/indicates that $R_2BX$ is employed in the presence of $R'_3N$.

2. An enolboration agent, bis(bicyclo[2.2.2.]octyl)iodoborane in the presence of triethylamine.

3. An enolboration agent, bis(bicyclo[2.2.2.]octyl)chloroborane in the presence of triethylamine.

* * * * *